(12) United States Patent
Adams

(10) Patent No.: US 10,330,571 B2
(45) Date of Patent: Jun. 25, 2019

(54) AIR SAMPLING SYSTEM

(71) Applicant: Alexander B. Adams, Bristol, TN (US)

(72) Inventor: Alexander B. Adams, Bristol, TN (US)

( * ) Notice: Subject to any disclaimer, the term of this patent is extended or adjusted under 35 U.S.C. 154(b) by 0 days.

(21) Appl. No.: 15/530,844

(22) Filed: Mar. 7, 2017

(65) Prior Publication Data

US 2018/0259429 A1     Sep. 13, 2018

(51) Int. Cl.
| | |
|---|---|
| G01N 1/22 | (2006.01) |
| G01N 33/00 | (2006.01) |
| B64C 39/02 | (2006.01) |
| B64D 1/00 | (2006.01) |

(52) U.S. Cl.
CPC ......... *G01N 1/2273* (2013.01); *B64C 39/024* (2013.01); *B64D 1/00* (2013.01); *G01N 33/0073* (2013.01); *B64C 2201/027* (2013.01); *B64C 2201/108* (2013.01); *B64C 2201/128* (2013.01); *B64C 2201/165* (2013.01)

(58) Field of Classification Search
CPC .............. G01N 1/2273; G01N 33/0073; B64C 2201/108; B64C 2201/128; B64C 2201/165; B64C 2201/027; B64C 39/024; B64D 1/00

See application file for complete search history.

(56) References Cited

U.S. PATENT DOCUMENTS

| | | | | |
|---|---|---|---|---|
| 3,077,779 | A | * | 2/1963 | Froehlich ............. G01N 1/2273 73/170.28 |
| 5,474,046 | A | | 12/1995 | Corona |
| 6,442,997 | B1 | * | 9/2002 | Megerle ............... G01N 1/2273 204/406 |

(Continued)

FOREIGN PATENT DOCUMENTS

| | | | | |
|---|---|---|---|---|
| DE | 102005025309 | B3 | * 12/2006 | ........... G01N 1/2208 |
| DE | 102007027326 | A1 | * 12/2008 | ............... G01N 1/24 |
| KR | 101716868 | B1 | * 3/2017 | |

OTHER PUBLICATIONS

Villa, Tommaso Francesco, et al. "An overview of small unmanned aerial vehicles for air quality measurements: Present applications and future prospectives." Sensors 16.7 (2016): 1072.*

(Continued)

*Primary Examiner* — Daniel S Larkin
(74) *Attorney, Agent, or Firm* — Robert J. Lauf

(57) ABSTRACT

An atmosphere sampling system includes:
    an unmanned rotary-wing aircraft platform including: an airframe capable of lifting a selected payload mass; at least one motorized rotor; and, a flight control system including an on-board controller;
    an atmosphere sampling unit having a total mass no greater than the selected payload mass, and including: a blower preferably having backward-facing blades, an inlet structure to draw in air to be sampled, and an outlet to discharge air after sampling; a plurality of sample containers; and, an indexing mechanism to move selected sample containers, one at a time, into contact with the inlet structure so that samples may be collected; and,
    a power supply with sufficient capacity to operate the motorized rotor(s), the onboard portion of the flight controller, the blower, and the indexing system.

7 Claims, 19 Drawing Sheets

(56) References Cited

U.S. PATENT DOCUMENTS

| | | | |
|---|---|---|---|
| 8,407,011 B2* | 3/2013 | Miller | G01N 1/26 702/19 |
| 8,820,672 B2* | 9/2014 | Erben | B64C 39/024 244/1 R |
| 9,170,178 B2 | 10/2015 | Sobek | |
| 2004/0118222 A1* | 6/2004 | Cornish | G01N 1/2252 73/863.22 |
| 2004/0185554 A1* | 9/2004 | Daitch | G01N 1/2273 435/309.1 |
| 2006/0123928 A1 | 6/2006 | Schimmoller | |
| 2010/0021288 A1* | 1/2010 | Collette | B64C 39/024 415/176 |
| 2011/0127421 A1* | 6/2011 | Finlay | G01N 30/72 250/283 |
| 2013/0030718 A1 | 1/2013 | Williams | |
| 2013/0278427 A1 | 10/2013 | Setton | |
| 2013/0292512 A1* | 11/2013 | Erben | B64C 39/024 244/1 R |
| 2014/0236390 A1 | 8/2014 | Mohamadi | |
| 2014/0303814 A1* | 10/2014 | Burema | A01B 79/005 701/3 |
| 2015/0040760 A1* | 2/2015 | Braden | G01N 1/2208 95/79 |
| 2016/0025603 A1 | 1/2016 | Kindt | |
| 2016/0161456 A1 | 6/2016 | Risk | |
| 2016/0169772 A1 | 6/2016 | Olmedo | |
| 2016/0200421 A1* | 7/2016 | Morrison | B64C 13/18 244/17.23 |
| 2016/0209382 A1* | 7/2016 | Shalom | G01N 1/2273 |
| 2016/0232794 A1 | 8/2016 | Hafeez | |
| 2016/0308954 A1 | 10/2016 | Wilbur | |
| 2016/0313744 A1 | 10/2016 | Amelio | |
| 2016/0364989 A1 | 12/2016 | Speasl | |
| 2018/0120227 A1* | 5/2018 | Ng | G01N 21/636 |
| 2018/0136093 A1* | 5/2018 | Avakov | G01N 1/2273 |

OTHER PUBLICATIONS

S. Patel and B. Little, "Power management trends, challenges in UAV apps", Texas Instruments, published Jan. 6, 2012, accessed online at <www.ti.com> on Jul. 2, 2018.*

"DR1000 Flying Laboratory, Drone Environmental Monitoring",Scentroid, Apr. 2017. Accessed online at <https://scentroid.com/wp-content/uploads/2017/04/DR1000-Brochure.pdf> pp. 1-13.*

* cited by examiner

AIR SAMPLING SYSTEM

BACKGROUND OF THE INVENTION

Field of the Invention

The invention pertains to apparatus and methods for collecting air samples, and more particularly to apparatus and methods for collecting air samples at known locations using a small unmanned aircraft.

Description of Related Art

There is an ongoing need for air sampling systems that are capable of being deployed remotely to sample stack emissions, plumes from gas or chemical leaks, dust or particulate plumes from stacks and dry conveyors, etc. More recently, interest has emerged in collecting a very specific type of particulate, viz., pathogenic cells, mold and mold spores, contaminated mists near air conditioning units and cooling towers, etc.

To consider one example, a recent report (Reuters News, September 2016) stated, "Corn mold lurks in U.S. fields, threatening crop yield." According to some estimates, mold may be responsible for destroying one-third of arable crops. This is more than a nuisance; it represents a serious economic loss to the farmer and to society in general.

The economic damage could be reduced by geolocating mold and providing these data to farmers. This would help farmers increase their yield by accurately locating mold in crop fields for effective mold remediation. Mold location data would allow farmers to reduce the risk associated with mold by implementing proactive risk management that allows farmers to treat the mold before damages occur. Ideally, a system should collect samples that can be identified later in the lab to provide the exact species of mold and recommend an optimal treatment strategy. An optimal strategy would use the mold location data to allow the farmer to treat only the infected area of the field, reducing the amount of fungicides used.

Small Unmanned Aircraft Systems (sUAS) operated under FAA's Part 107 have begun to be used to collect samples of various kinds. In one approach, a multi-rotor drone carries an inflatable sample bag that can be filled with an air sample for later analysis [Scentroid DR1000 Flying Laboratory, 431 Alden Rd. #3, Markham, Ontario, Canada]. It will be appreciated, however, that collecting particulates, especially biological samples, is more difficult than simply inflating a small, collapsible bag. Typically, a significant volume of air must be drawn through a porous capture medium, which might be a sheet of filter paper or a wad of fibrous material, so that the total number of spores or cells contained in that volume of air may be concentrated into a small sample for examination, analysis, or culture. Such filter-based air samplers typically employ positive-displacement (piston-type) pumps, which are inherently very heavy machines and generally unsuitable for deployment on low-cost rotary-wing sUAS, which typically have very limited payload capacity.

Objects and Advantages

Objects of the present invention include the following: providing a robust, user-friendly system for remote air sampling; providing a particulate sample collection system that is light enough to be deployed on a small unmanned aircraft system; providing a system for geolocating mold or other pathogens; providing a system to collect and archive multiple samples of pathogenic particulates at preselected locations for later analysis; and providing an airborne sample collection system that may be operated in real time from the ground or operated to autonomously follow a preprogrammed flight plan. These and other objects and advantages of the invention will become apparent from consideration of the following specification, read in conjunction with the drawings.

SUMMARY OF THE INVENTION

According to one aspect of the invention, an atmosphere sampling system comprises:
  an unmanned rotary-wing aircraft platform comprising:
    an airframe capable of lifting a selected payload mass;
    at least one motorized rotor; and,
    a flight control system including an on-board controller;
  an atmosphere sampling unit having a total mass no greater than said selected payload mass, and comprising:
    a blower having backward-facing blades, an inlet structure to draw in said atmosphere to be sampled, and an outlet to discharge said atmosphere after sampling;
    a plurality of sample containers, each having a porous sample collecting medium therein; and,
    an indexing mechanism to move selected sample containers, one at a time, into contact with said inlet structure so that samples may be collected on said porous medium; and,
  a power supply with sufficient capacity to operate said motorized rotor(s), the onboard portion of said flight controller, said blower, and said indexing system.

According to another aspect of the invention, an atmosphere sampling system comprises:
  an unmanned rotary-wing aircraft platform comprising:
    an airframe capable of lifting a selected payload mass;
    at least one motorized rotor; and,
    a flight control system including an on-board controller;
  an atmosphere sampling unit having a total mass no greater than said selected payload mass, and comprising:
    a blower having backward-facing blades, an inlet structure to draw in said atmosphere to be sampled, and an outlet to discharge said atmosphere after sampling;
    at least one sample analyzer upstream of said inlet structure and including a sensor for measuring at least one characteristic of said atmosphere as it flows through said analyzer; and,
    a power supply with sufficient capacity to operate the motorized rotor(s), the onboard portion of the flight controller, the blower, and the sample analyzer.

According to another aspect of the invention, a method for atmospheric sampling comprises the steps of:
  mounting an atmospheric sampling device to a small unmanned aircraft system (sUAS) that is capable of moving from one location to another and hovering at selected locations for selected times;
  directing said sUAS to one or more selected location(s);
  keeping said sUAS at each of said selected location(s) for a sufficient time to allow a sample to be collected;
  obtaining geolocation data corresponding to each of said location(s) so that each sample may be associated with the location in which it was collected.

BRIEF DESCRIPTION OF THE DRAWINGS

The drawings accompanying and forming part of this specification are included to depict certain aspects of the invention. A clearer conception of the invention, and of the components and operation of systems provided with the invention, will become more readily apparent by referring to the exemplary, and therefore non-limiting features illustrated in the drawing figures, wherein like numerals (if they occur in more than one view) designate the same elements. The features in the drawings are not necessarily drawn to scale.

DETAILED DESCRIPTION OF THE INVENTION

In its most general sense, the invention comprises a small unmanned aircraft platform carrying an air sampling system, including multiple sampling cartridges, or a single testing chamber, that can fly from one selected sampling location to another, either autonomously or under remote control, and return the sample cartridges for later analysis or collect data in flight for later analysis. Various aspects of the invention will be described in more detail in the exemplary materials that follow.

Example

Unmanned Aircraft System

Figure 1:
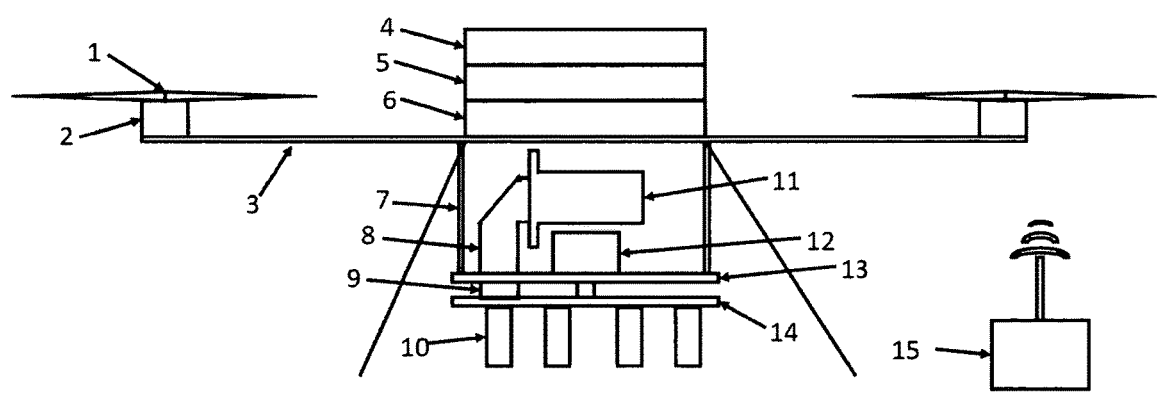
FIG. 1 is a schematic diagram of one example of the present invention showing the preferred components of a functional system.

One suitable sUAS-based delivery system, illustrated schematically in FIG. 1, is a custom built octocopter that is operated under FAA's Part 107 as a sUAS (Small Unmanned Aircraft System). The octocopter consists of the following components: one airframe 3 [Tarot Model T18 Frame, No. 1, Puzhou Phase III Industrial Zone, Lucheng District Wenzhou City, Zhejiang Province, China], eight brushless motors 2 [Tarot Model 5008], eight carbon fiber propellers 1 (two are shown) [Tarot Model 1855], eight electronic speed controllers (part of module 5 for the controller aspect, but also part of 6 because it supplies power to the motors)) [FlyFun 60A, Hobbywing, Building 4, Yasen Chuangxin Hi-tech Industrial Park, 8 Chengxin Road, Baolong Industrial Town, Shenzhen, China], power supply 6 containing two batteries [Graphene 16000 mAh 22.2v, Turnigy, Block B, 2 Floor, Merit Industrial Center, 94 Tokwawan Road, Tokwawan, Kowloon, Hong Kong], flight controller 5 [Pixhawk, 3DR, 1608 4th Street, Suite 410, Berkeley, Calif.], two voltage regulators with 3 amps at 5.30 volts output, [Mauch Electronics, 177 Mei Ai Lu, Baoshan Qu, Shanghai Shi, China], handheld radio transmitter 15 [Taranis X9D, FrSky, F-4, Building C, Zhongxiu Technology Park, No. 3 Yuanxi Road, Wuxi, 214125, Jiangsu, China], radio receiver (part of module 4) [X8R, FrSky], two receivers [NEO-M8N Triple Band receiver with EMI protection and HMC5983 Compass PRO version, CSG Shop, http://www.csgshop.com/], and radio modem (would be part of 4 and 15) [RFDesign Model 900+, Unit 7/1 Stockwell Place, Archerfield, Queensland, Australia].

The software that controls the octocopter from the 3DR Pixhawk flight controller is Ardupilot. Mission Planner, a free and open source software ground station application, was downloaded onto a computer. The ArduCopter, a specific version of ArduPilot, firmware was then installed onto the 3DR Pixhawk through the Mission Planner software. The complete instructions on installing ArduCopter using Mission Planner can be found at http://ardupilot.org/planner/index.html. It should also be noted that ArduCopter could be installed with similar ground station applications: APM Planner 2, MAVProxy, QGroundControl, and Universal Ground Control Station.

The invention may further include a "companion computer", which is a device that travels on board the sUAS and allows developers to create powerful applications, using onboard computing, that communicates with the flight controller. Companion computers typically run computation intensive programs or time-sensitive tasks such as intelligent path planning, computer vision, and 3D modeling. Companion computers can also add the benefit of running additional sensors or actuators that cannot be controlled through the flight controller. An alternative approach would be to process the information at the ground control station or cloud then resend the computed information back to the drone while stationary or inflight. The user can select the most appropriate computational approach depending on routine engineering considerations such as mission time, complexity, on-board computing capacity, and data processing requirements.

As used herein, the term "flight controller" is intended broadly to include any of the following: on-board data processors, companion computers, and cloud or ground control computer processing, as the geolocation data could be recorded in any of these locations.

Example

The sUAS described above has a flight time of roughly 32 minutes (20% of battery remaining) when hovering out of ground effect with zero payload. The sUAS has a mass of roughly 9 kg and can carry a maximum payload of 12.7 kg. The flight endurance at gross weight was not determined.

Example

Air Sampler

An air sampler, FIGS. 2 and 3, was designed to be suspended below the sUAS-based delivery system via supports 7 and base plate 13 on rails that are integrated into the Tarot T18 Frame. The sampler consists of a sampling cartridge 10, a 9-sample rotary cartridge holder 14, driven by servo 12 [S125 Digital Servo, GWS, 1F., No. 125, SEC. 2, Datung Road., Shijr City, Taipei 221, Taiwan], a 12-volt centrifugal blower 11 [Quick-Fill 080, Intex, 1665 Hughes Way, Long Beach, Calif.], voltage regulator 31 with 5 amps at 5 volts and 10 amps at 12 volts outputs (may be part of 31 or incorporated into the blower module 11), [Multistar, Turnigy, Block B, 2 Floor, Merit Industrial Center, 94 Tokwawan Road, Tokwawan, Kowloon, Hong Kong], and a receiver-controlled switch [Turnigy, Kowloon, Hong Kong].

Each sampling cartridge 10 attaches to the rotary cartridge sampler (revolver) 14 which can hold a total of 9 cartridges. The cartridge is then indexed into position proximate to blower intake pipe 8 and connecting pipe 9 using the GWS S125 Digital Servo 12 below the centrifugal blower by receiving a signal from the 3DR Pixhawk flight controller 5. Once the sample has been indexed, the Turnigy receiver-controlled switch turns on the centrifugal blower 11 once it receives the signal from the 3DR Pixhawk to begin taking a sample. The exhaust air from the centrifugal blower then cools the Turnigy Multistar Voltage Regulator 31 with 5 A at 5 V and 10 A at 12 V outputs. The process is then repeated by the 3DR Pixhawk flight controller 5 sending a signal to turn off the blower and index the rotary cartridge holder to the next position.

The goal for the sampler design was to have a high flow rate while maintaining a high static pressure to be able to move the air across the sampling cartridge. Applicant recognized that the main limiting factor to the design was weight followed by power consumption. Weight is the main limiting factor because the sUAS, as described above, uses roughly 120 watts/kg to hover even if the blower is not operating. Developing a light weight sampler was therefore crucial in order to have a sUAS that could have a long endurance and be able to lift the payload.

The power consumption needed to be limited because the lightweight electronics needed to run the centrifugal blower become extremely limited above 10 A for off the shelf components. Also, all sUAS applications must consider the current required by the blower in order to keep the current within the specified current that the battery can discharge safely, and within the voltage regulator specifications, if applicable. The current the battery can safely discharge is in turn dependent on the battery specification (make, cells, voltage, type, etc.).

The target time per air sample was roughly 1 minute which would require a volume of 150 liters to flow through the sample cartridge [mTrap, Assured Bio Labs, 228 Midway Lane, Suite B, Oak Ridge, Tenn.].

Fan and Blower Considerations

The baseline samplers in the mold industry are piston-type positive displacement compressors. Two examples of the baseline pump are: 1) Environmental Monitoring Systems' MegaLite IAQ Pump, which has a flow rate of 30 liters per minute (LPM) with a mass of 2.5 kg and is powered at 115 V and 0.46 A; and 2) Zefon's Z-Lite IAQ Air Sampling Pump, which has a flow rate of 30 LPM with a weight of 3.6 kg. When a technician is sampling with these types of pumps they take roughly 5 minutes to collect a sample when sampling at 30 LPM, assuming a sample of 150 liters is needed for the mTrap cartridge. The heavy weight of 2.5-3.6 kg for these two examples would significantly reduce the sUAS flight time for the air frame and power supplies described in the previous example. The low throughput of these two candidates ruled out the industry standard for sUAS applications since the sUAS has a flight time of roughly 32 minutes down to 20% battery remaining. The low throughput would not allow enough samples to be taken per flight for sampling to be cost effective over large areas.

Based on the fact that positive displacement pumps were deemed to adversely limit performance, Applicant undertook research into axial fan designs because of their high flow rate and relatively low power consumption. Applicant quickly discovered that such axial fans are considered generally unsuitable for use as a vacuum pump. What this means is that fans are traditionally designed to operate with the inlet open to the atmosphere, i.e., with no restriction or pressure drop at the inlet side, and to provide flowing air at the outlet side. Applicant, by contrast, sought to place the sampling cartridge, i.e., the flow restriction, on the inlet side of the fan and thereby utilize a blower as a suction pump and not as it was intended to be used. The sampling cartridge needed to be placed on the inlet side of the pump to reduce the risk of preexisting contaminants inside the pump housing from contaminating the sample, which would give a false reading.

FIGS. 7-17 illustrate various configurations of fans in order to make the discussions that follow more clear.

Example

Figure 7:
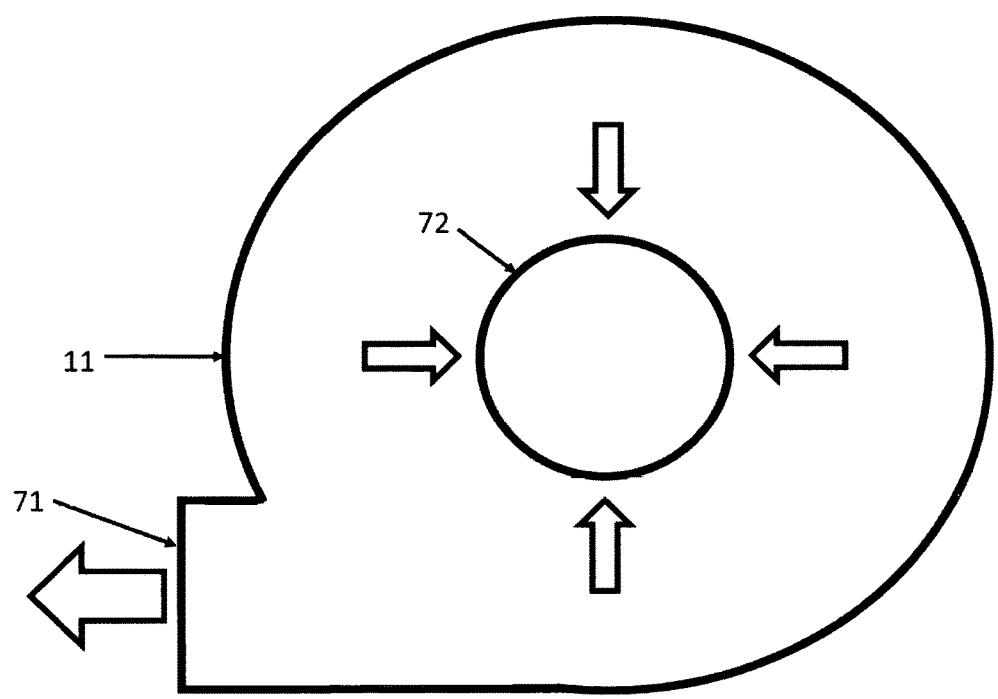
FIG. 7 is a schematic diagram of a blower casing configuration and the resulting airflow in accordance with one aspect of the invention.
Figure 8:
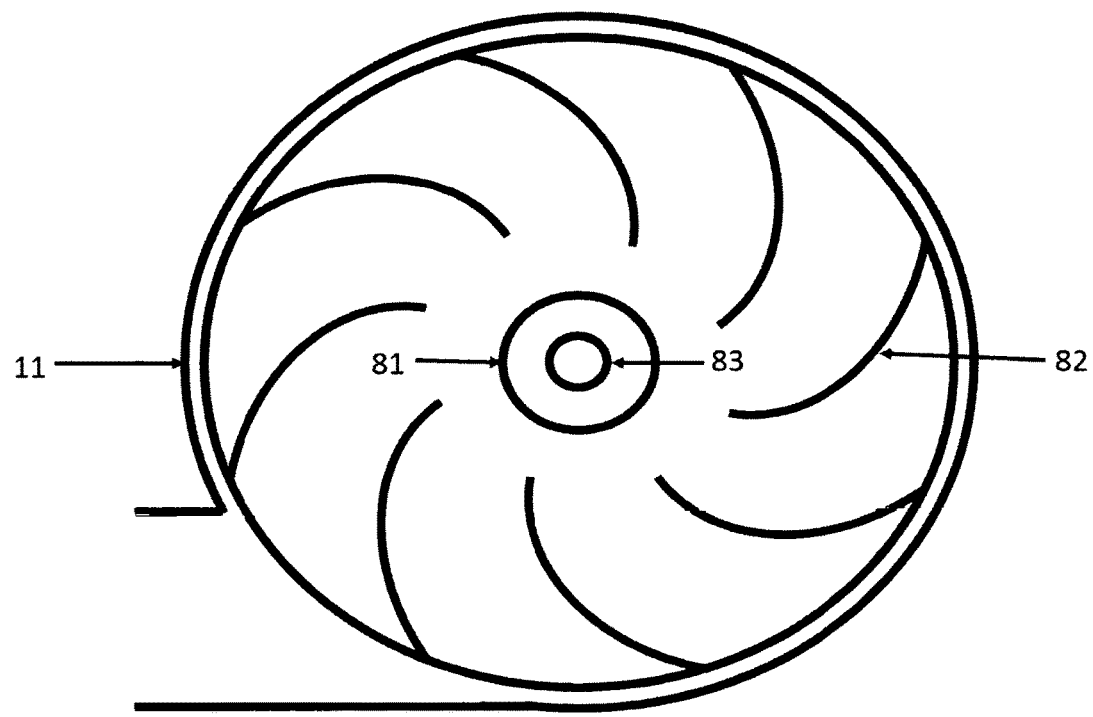
FIG. 8 is a schematic diagram of the internal configuration of the blower in the previous figure.

The first attempt to adapt an axial fan, FIG. 7, to this problem used a fan [Corsair SP120 High Performance Edition, 47100 Bayside Parkway Fremont, Calif.], which had an airflow of 62.74 cubic feet per minute (CFM), Static Pressure of 3.1 mm $H_2O$, and a Power Draw of 0.18 A at 12 V. When the Corsair axial fan was fitted to the sample cartridge, it yielded no measurable air flow through the sample cartridge, because the static pressure wasn't high enough to overcome the resistance caused by the sample cartridge. With such a low airflow from such a relatively high performance axial fan, the axial fan design was rejected. The Corsair SP120 High Performance fan had a mass of 0.2 kilograms.

Figure 9:
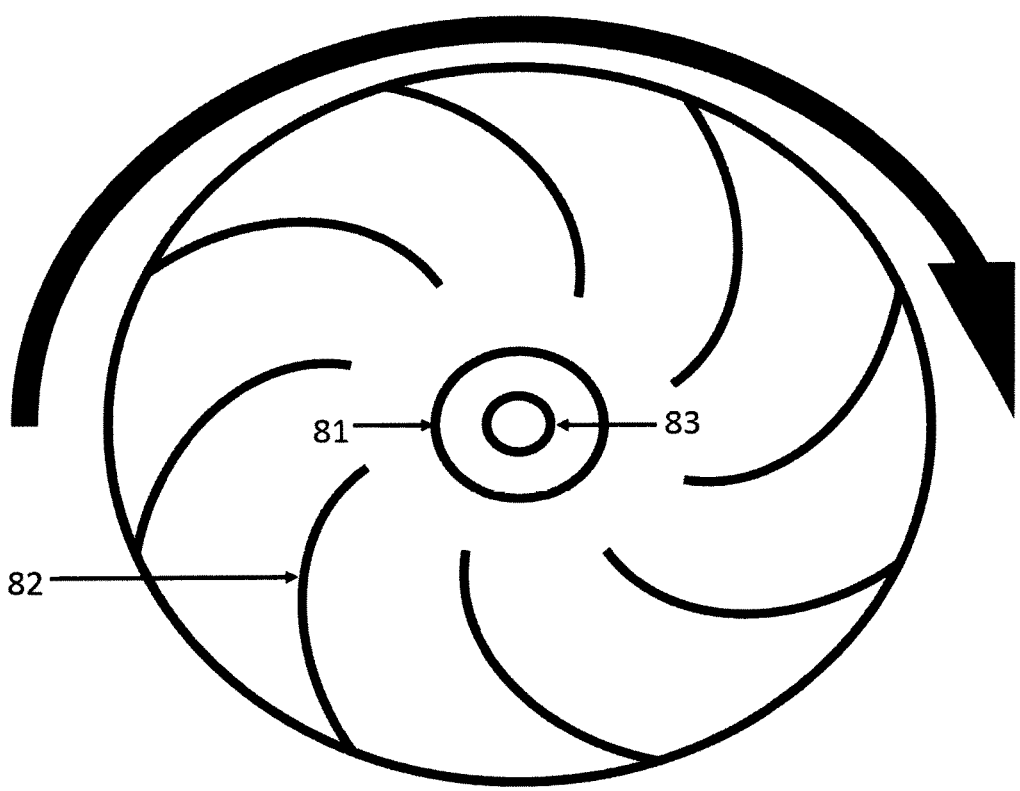
FIG. 9 is a schematic diagram of a blower having a backward-facing blade (arrow indicates the direction of rotation).
Figure 10:
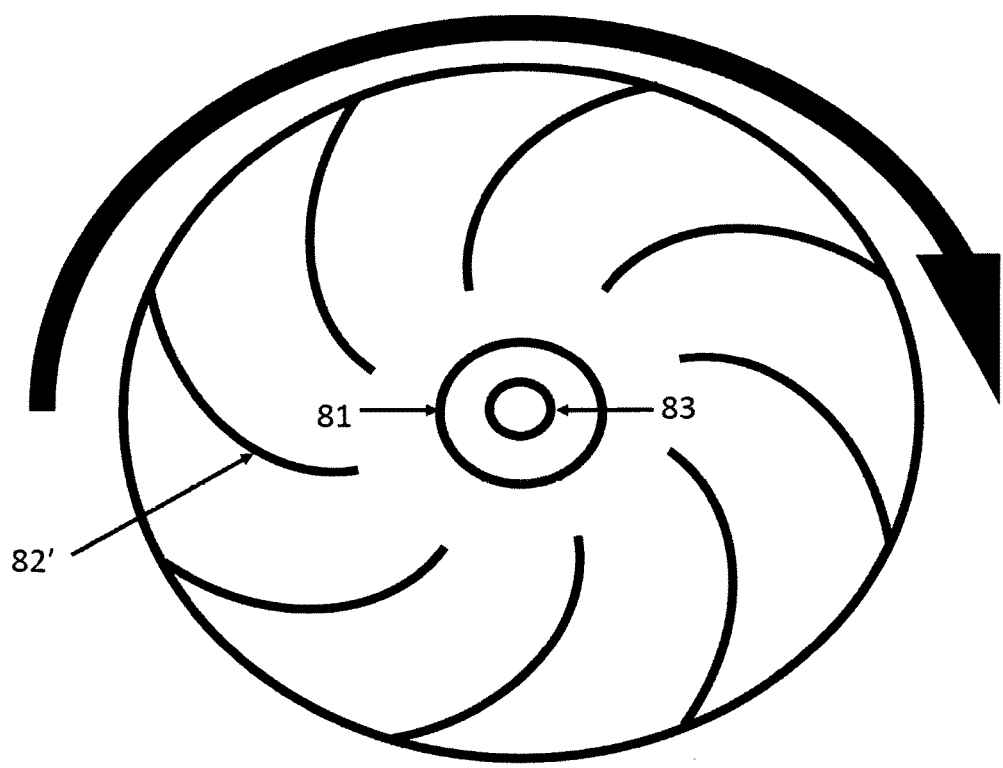
FIG. 10 is a schematic diagram of a blower having a forward-facing blade.
Figure 11:
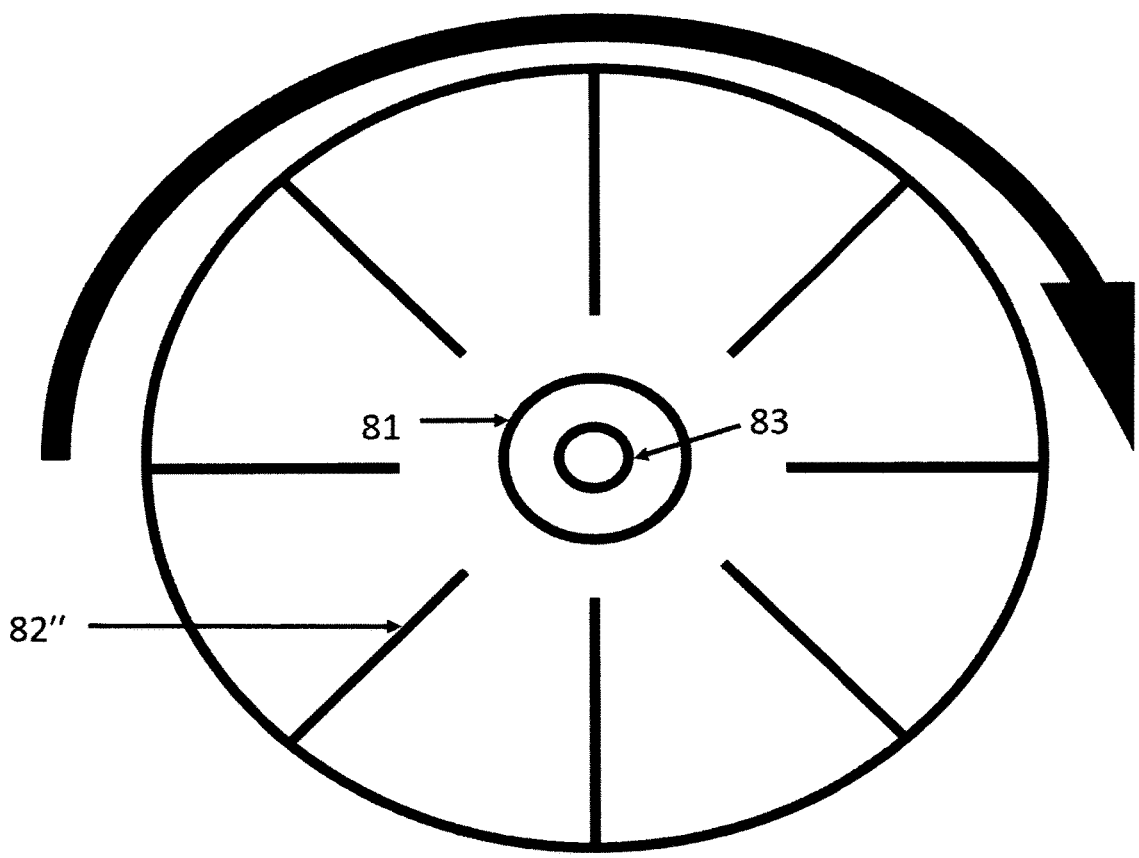
FIG. 11 is a schematic diagram of a blower having radial blades.

Applicant postulated that a centrifugal blower in backward facing blades, FIG. 9, might be better suited for sUAS applications because of their increased efficiency over radial (FIG. 11) or forward (FIG. 10) facing blades. Backward facing blades also produce a high flow rate at a high pressure and will not overload with changes in static pressure, possibly allowing for a variety of sampling cartridges to be used, with varying flow restrictions, with a single blower design.

Example

The first centrifugal blower with backward facing blade to be selected for trial was the Model BFB04512HD [Delta Electronics, 252 Shang Ying Road, Kuei San Industrial Zone, Taoyuan Shien, Taiwan], which is a backward facing blade design that does not have a shroud connected to the blades. According to the manufacturer's specifications it is cable of flowing 138.8 liters per minute (LPM) and a static pressure of 9.3 mm $H_2O$. The power consumption is 12V at 0.1 A.

Applicant inquired with the manufacturer for information on the performance of the aforementioned blower when configured to be run as a suction device (i.e., with a restriction on the intake side and the outlet free to ambient air) and was advised by the manufacturer that "our blowers cannot be run as a vacuum."

Example

Despite the manufacturer's recommendation to the contrary, Applicant fitted the BFB0512HD blower to the sample cartridge, and discovered, surprisingly, that it achieved a flow rate of 1.3 LPM. This was a drastic improvement over the Corsair axial flow fan, providing a larger flow rate with a lower power consumption.

Based on this discovery that a blower could be adapted to the sampling problem, Applicant began testing different blower designs and configurations.

Example

Figure 12:
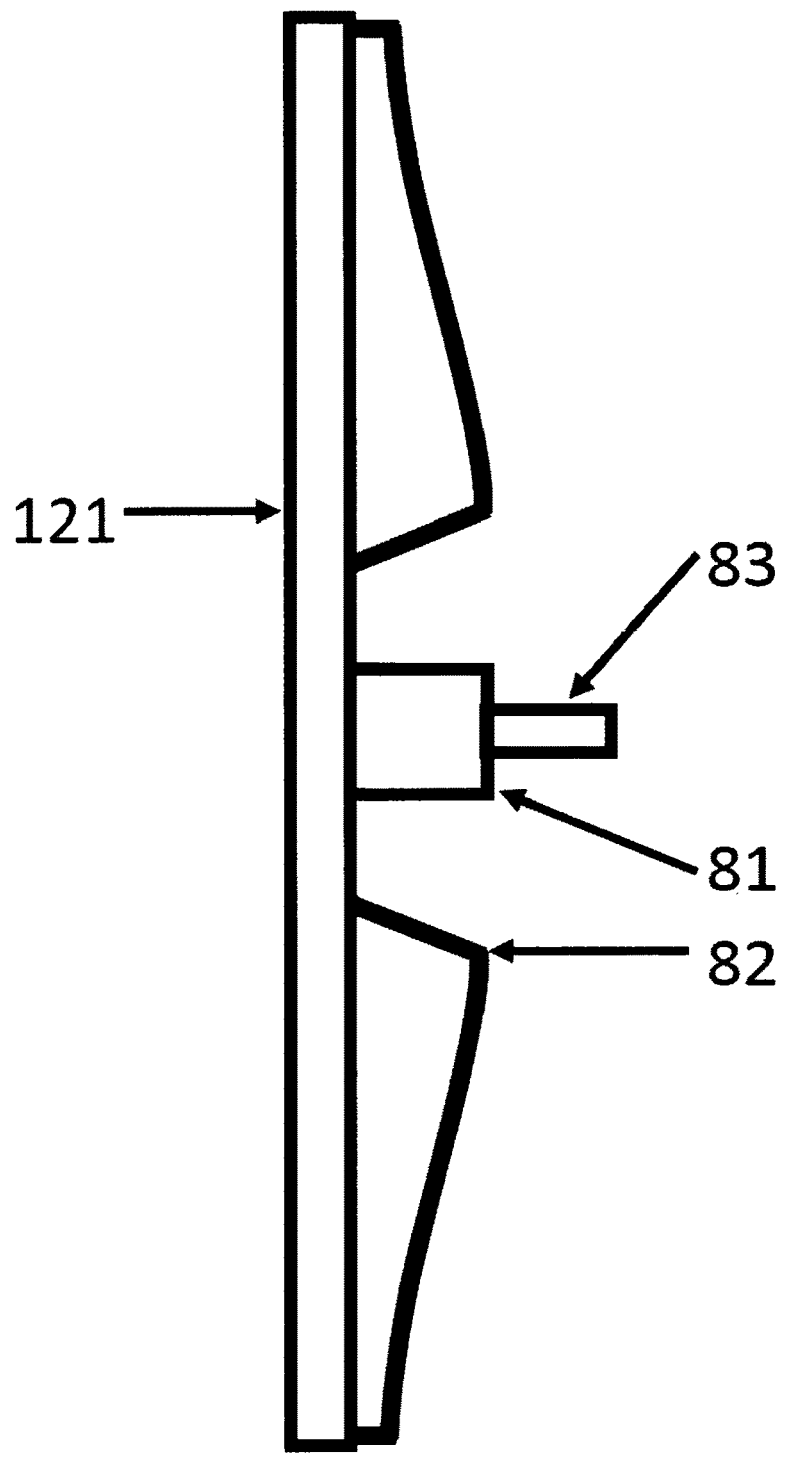
FIG. 12 is a schematic diagram of a blower in side view.
Figure 13:
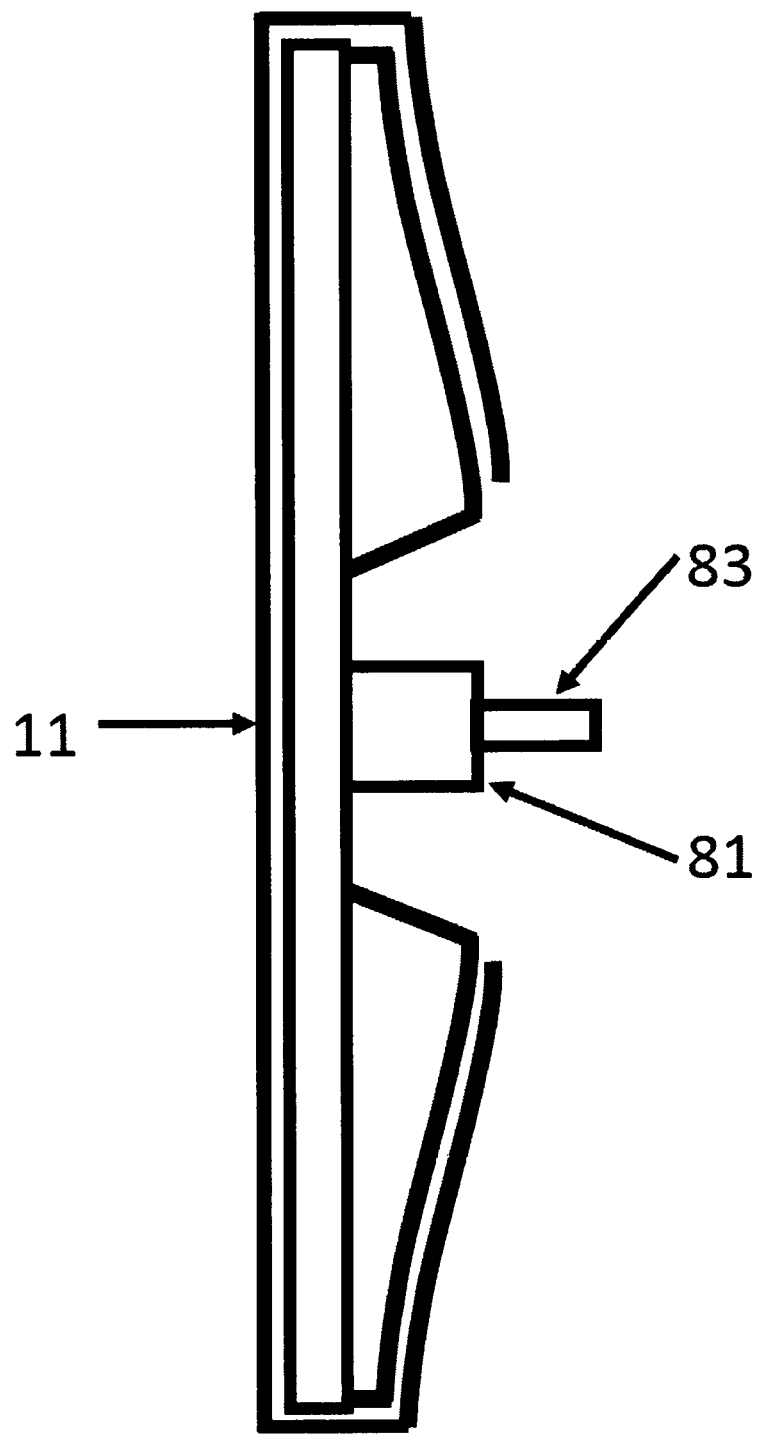
FIG. 13 is a schematic diagram of the blower in the previous figure with its associated casing.
Figure 14:
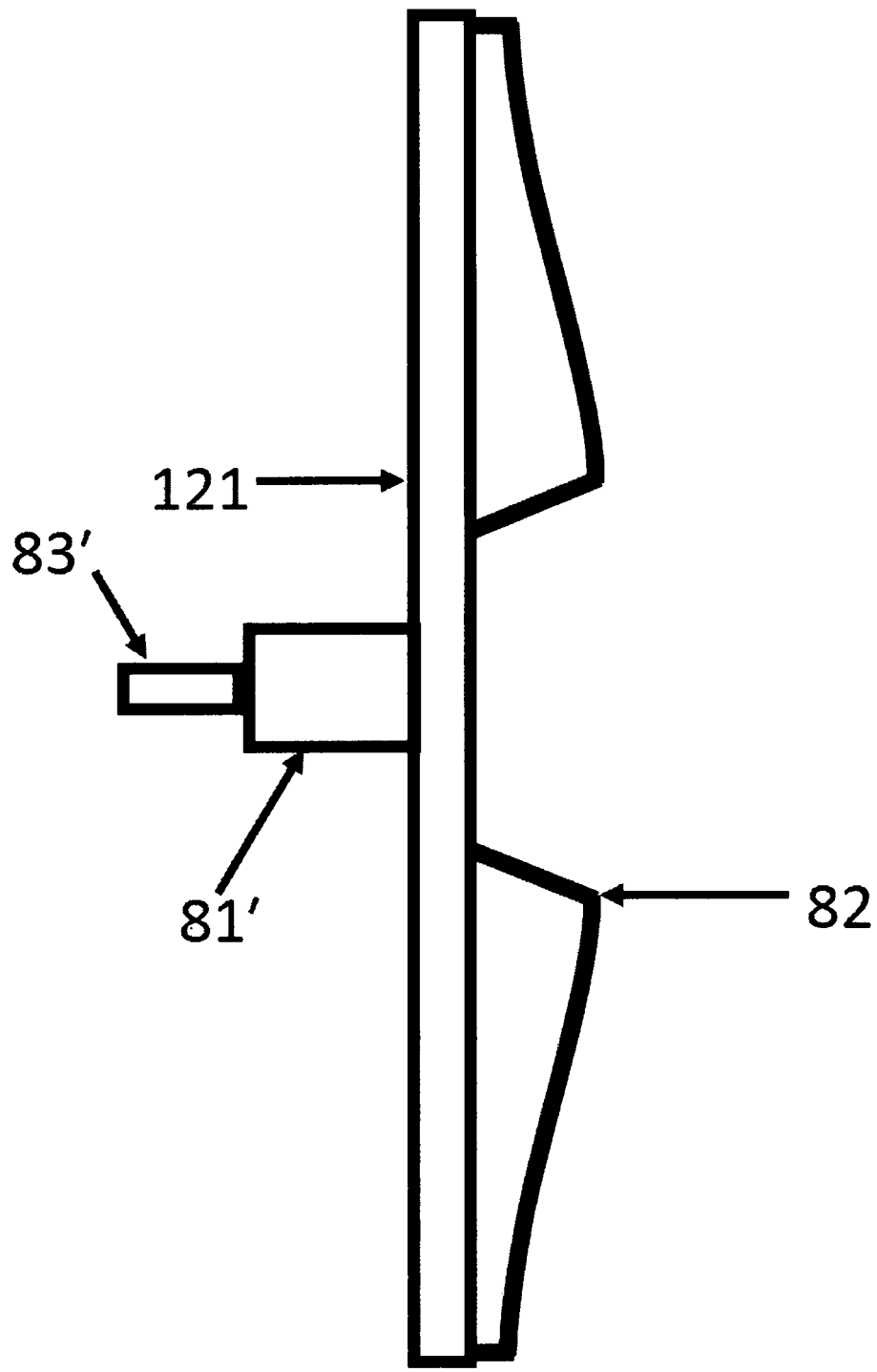
FIG. 14 is a schematic diagram of a blower having a single shaft on the rear side.

To maximize the efficiency of the centrifugal blower, the backward facing blade was equipped with a completely enclosed shroud 121 attached to the blades on one side and open on the other as shown generally in FIG. 12. Having the fully-closed shroud attached to the blades on only one side not only improves efficiency but also allows for easy cleaning of the blades if the blower becomes contaminated since one side is open. A centrifugal blower that met this description was the Intex Quick-Fill 080 pump that is powered at 12 V at 8 A and normally intended to be used to blow air into inflatable mattresses and the like, with its inlet side open to ambient pressure. The factory specification for this pump is 600 LPM and a static pressure of 323.41 mm $H_2O$. When tested in the lab with the mTrap sample cartridge in place the Intex pump produced a flow rate of at least 50 LPM. The blower had a mass of 1.2 kg.

Example

Figure 15:
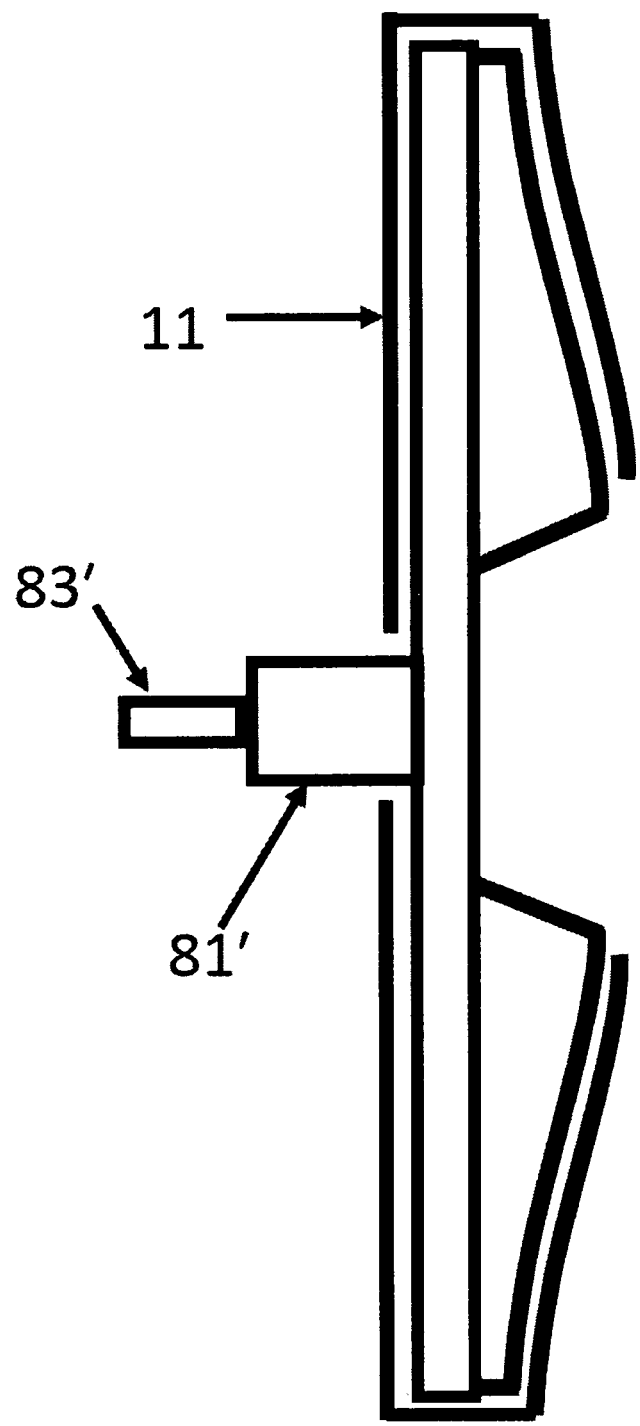
FIG. 15 is a schematic diagram of the blower in the previous figure with its associated casing.
Figure 16:
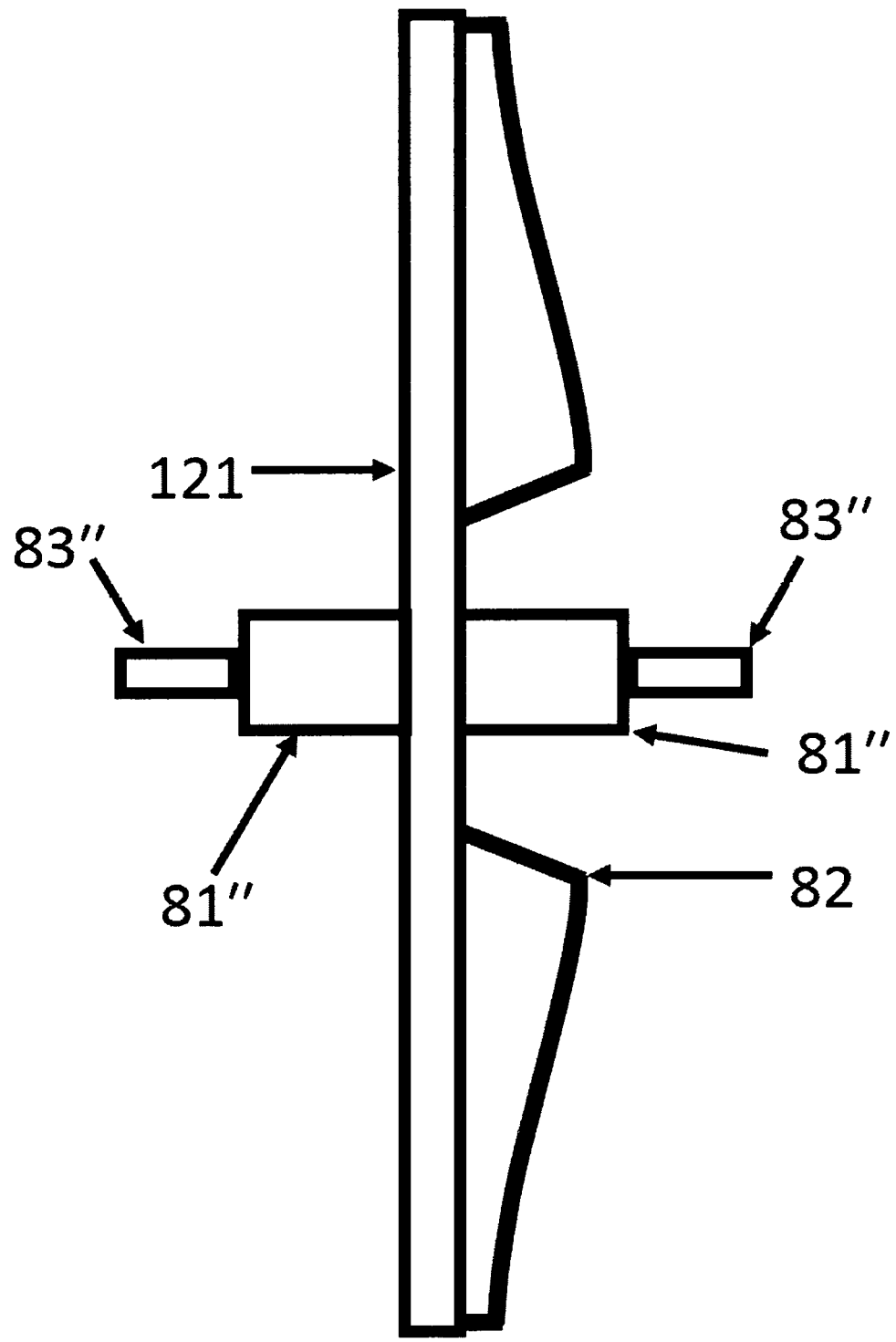
FIG. 16 is a schematic diagram of a blower with a drive shaft accessible from either side.
Figure 17:
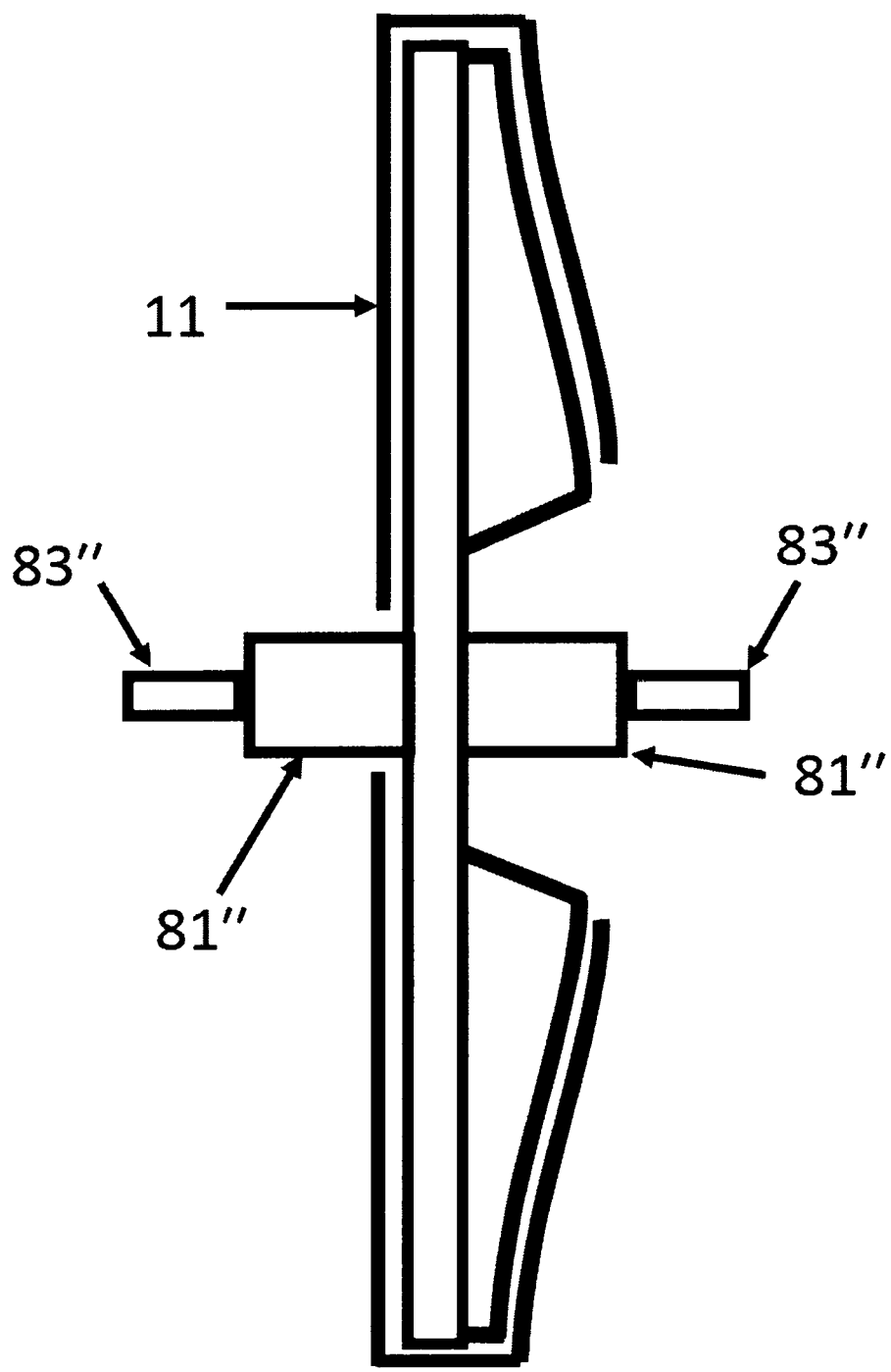
FIG. 17 is a schematic diagram of the blower in the previous figure with its associated casing.

Several additional features of the blower are shown schematically in FIGS. 12-17. The drive shaft 83, 83', 83" is held in a hub 81, 81', 81", and may extend on either or both sides of the fan itself. In the example shown in FIG. 1, shaft 83 is driven directly by a motor contained within an integral housing, but it will be appreciated that the shaft might be belt-driven if that design might allow more convenient placement of various components on a particular airframe. Blower case 11 may be provided with a hole on the back side as shown in FIGS. 15 and 17 to accommodate the shaft and hub if the drive is placed on the back side.

Example

One application for the invention is for sampling airborne mold. For this task, the sampler was configured to use a cartridge as generally described in U.S. Pat. No. 9,170,178. One suitable cartridge is Assured Bio Labs mTrap. The mTrap works by capturing pathogens or particulates by blowing the atmosphere across a filter.

It will be appreciated that many other air sampling problems exist, for which the invention may be adapted by using other kinds of sample cartridges. For example, a cartridge containing gold or copper wool could be used to collect airborne mercury vapor for monitoring emissions from mines, power plant stacks, and other potential sources of elemental Hg emissions. Activated carbon could be used to capture radon or various chemicals, particularly organics. Air sampling around cooling towers could be used to detect not only mold but also very fine water droplets for analysis to detect *Legionella* or other pathogenic microbes. Furthermore, filtration per se, is not the only means to capture a sample; inertial impaction or deposition onto a tacky or adhesive surface may also be used, as, for example, in the Air-O-Cell® sampling cassette (Zefon International, Inc., 5350 SW 1st Lane, Ocala, Fla. 34474). Other means of sample collection can include sedimentation, impingement, impaction, slit-to-agar impactors, sieve impactors, centrefugil impactors, and membrane filtration. The skilled artisan may adapt the invention to such applications and variants using routine experimentation.

Figure 18:
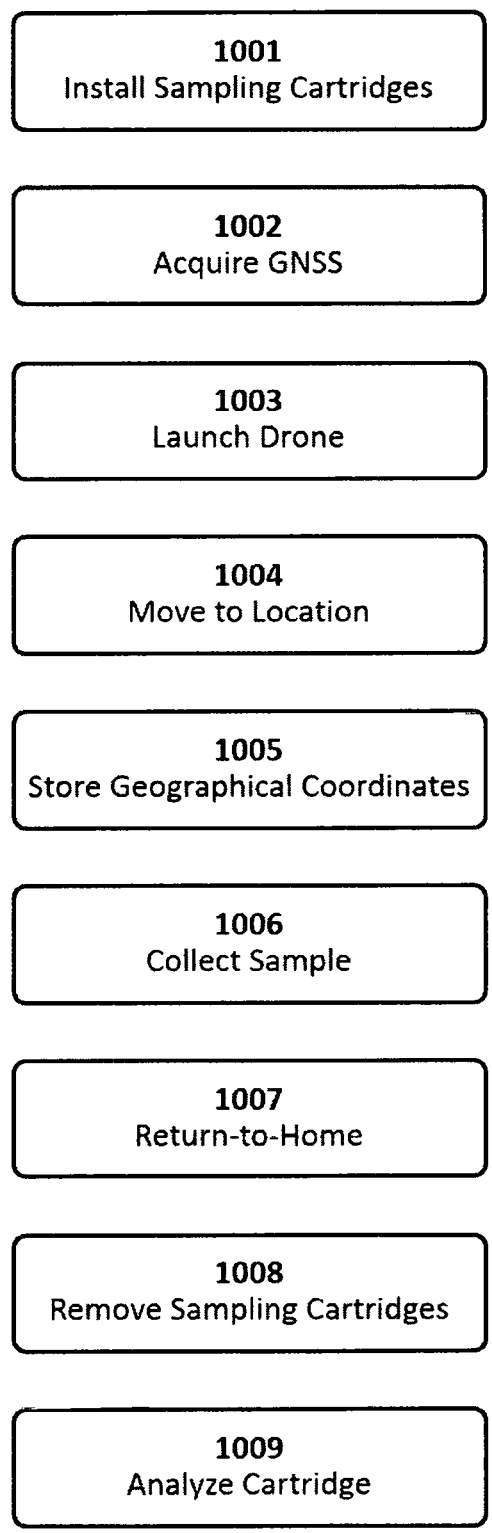
FIG. 18 is a schematic diagram of the steps in a sampling mission in accordance with one aspect of the invention.

As noted previously, a typical mission is contemplated to consist of maneuvering the sUAS into position at selected places that define a sampling pattern, keeping the sUAS in each place while drawing a predetermined amount of air through one sample cartridge, then indexing to another cartridge and moving to another place, and so on until the entire supply of cartridges has been filled with samples, then returning to base so that the cartridges can be removed for analysis. The steps of the method are shown schematically in FIG. 18. It will be appreciated that steps 1004-1006 will be repeated for each sample collected during the mission.

Example

Figure 2:
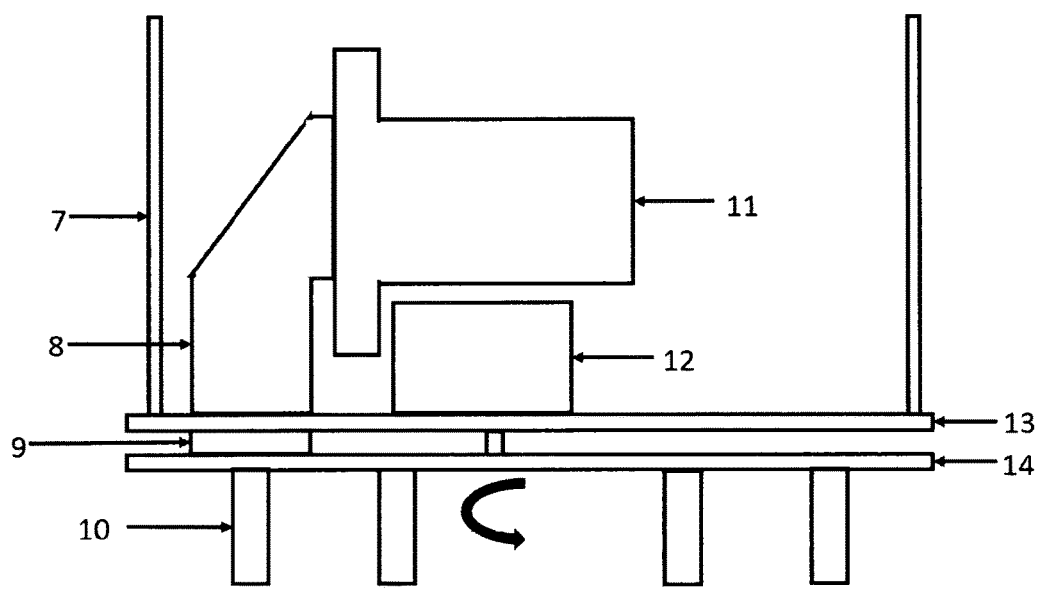
FIG. 2 is a schematic diagram of a sampling system in accordance with another aspect of the invention.
Figure 3:
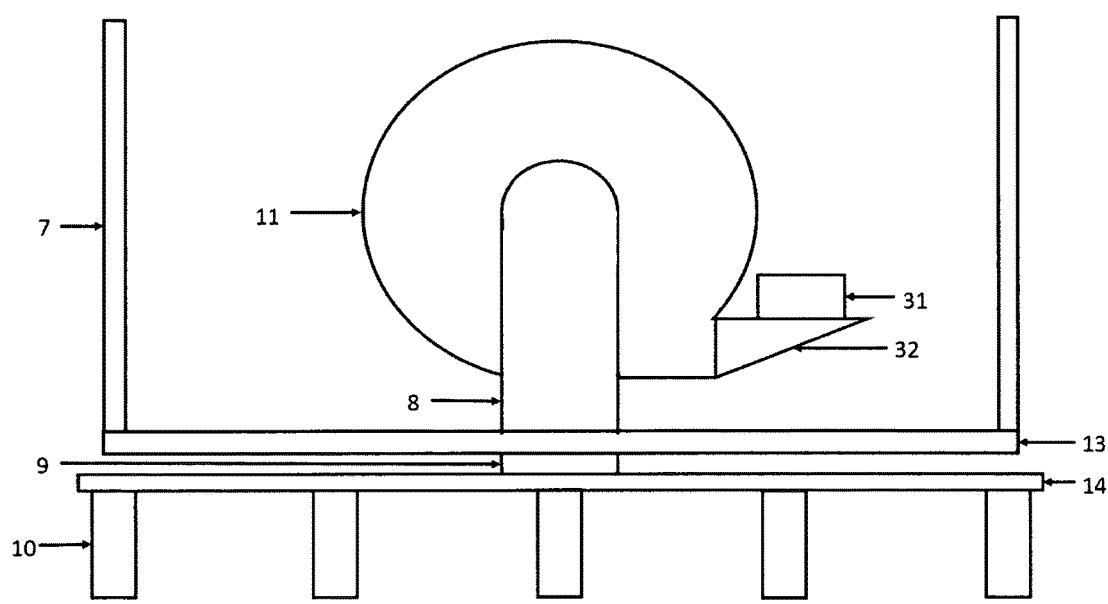
FIG. 3 is a schematic diagram of the same sampling system, viewed in an orthogonal direction relative to the previous view.

One suitable method for accommodating multiple samples is a circular carousel, as shown generally in FIGS. 1-3, that is indexed by rotation from one index position to the next as indicated by the curved arrow in FIG. 2. The circular carousel method eliminates the change in center of gravity (CG), allowing for constant flight characteristics and keeps the CG within the aircraft specifications. It will be appreciated, however, that other means exist to achieve the same purpose.

A square or rectangular array plate may be constructed to hold the cartridges. The plate would be slidably mounted so that X-Y actuators or steppers may index sequentially from one sample to the next.

Figure 4:
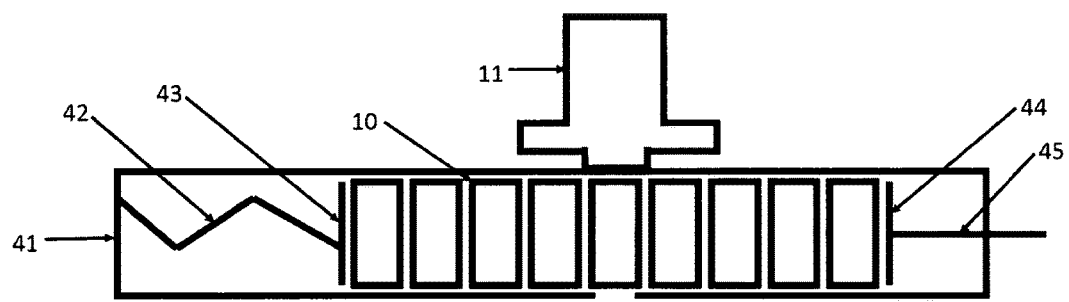
FIG. 4 is a schematic diagram of a linear magazine containing sampling cartridges.

The cartridges may be mounted in a single row in a magazine 41 similar to an ammunition magazine as shown schematically in FIG. 4. An actuator 44-45 may be placed at one end of the magazine and each cartridge 10 may be advanced in turn, with a spring 42 in the other end (dead space) of the magazine to work against the actuator and keep the cartridges in place. Openings on the top and bottom of the magazine would allow the air to flow through the particular cartridge that is under the pump assembly 11.

Figure 5:
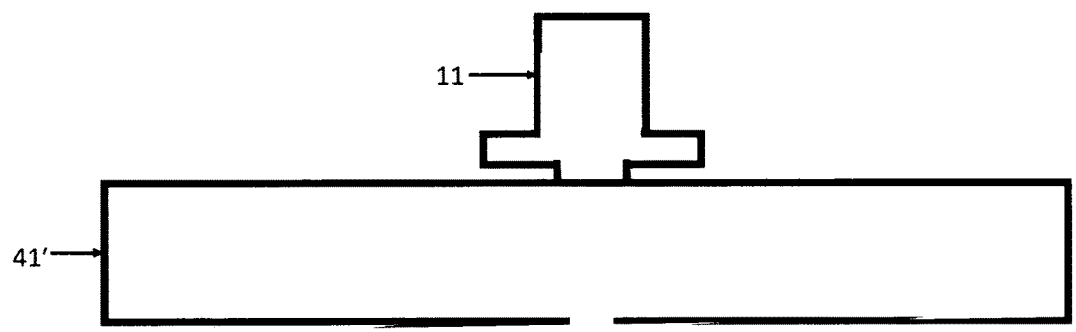
FIG. 5 is a schematic diagram of a drum-type magazine for handling a plurality of sampling cartridges.
Figure 6:
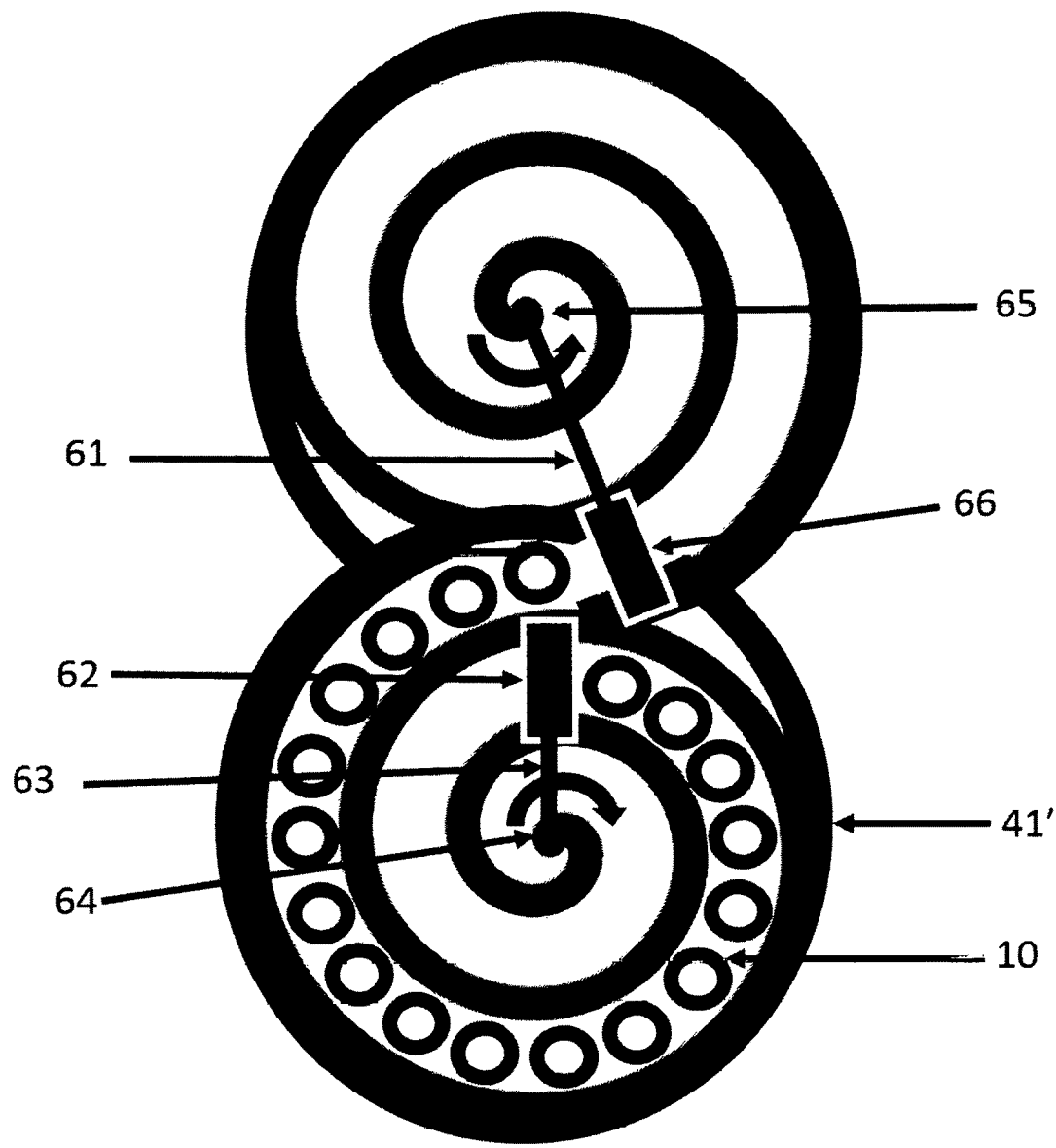
FIG. 6 is a schematic diagram in cross section of a drum-type magazine showing one arrangement of cartridges therein.

The cartridges may be mounted in two spirals in a magazine 41' similar to a dual-drum ammunition magazine as shown schematically in FIGS. 5-6. The driving spiral drum would have a servo 64 connected to a telescoping arm 63. The telescoping arm would rotate the cartridge plate 62, tracking along the spiral. As the telescoping arm rotated, it would index the cartridge 10 into position. The expended cartridges would then be indexed into the unloading drum while compression is applied to the cartridges via unloading spring 65, unloading telescoping arm 61, and unloading cartridge plate 66. It is noted that existing ammunition drum magazine design principle could be adapted for the use of sample cartridges. One such device is the familiar Soviet-era PPSh-41 drum magazine.

Example

The sUAS can be controlled manually by a ground station 15 or programmed before launch so that the entire mission can be conducted autonomously.

The ground station consists of two parts that can be run simultaneously or independently, the handheld transmitter and/or application running on a laptop or other device. The handheld ground control requires full manual control of the sUAS to conduct a flight and requires the operator to have existing sUAS experience. Using the handheld ground control however does not require the use of GPS since the aircraft is being flown visually within line of sight.

The application on a laptop or other device does not require any sUAS experience, it does however require the use of a GPS. The pilot operates the sUAS from the laptop by clicking on commands in the application and clicking on locations on a downloaded map to fly to a given waypoint at a given altitude. Both the handheld and laptop parts of the ground station send telemetry on independent radio frequencies, some of the information includes battery voltage, power consumed, altitude, ground speed and distance from home location.

The sUAS can fly fully autonomously without the use of a ground station after it is launched, even though contact with a ground station is recommended, by uploading data to the flight controller before launch. The flight plan is created in the application by setting a home location, waypoints, actions at waypoints, takeoff actions, and landing actions. The flight plan data is then transferred to the sUAS via a USB cable or a radio modem and stored on the flight controller memory.

It will be understood that Applicant's use of the term "autonomously" simply implies that the sUAS is navigating from place to place without the real-time intervention of a ground controller. The skilled artisan will be aware that terminology in the field may vary, e.g., some authors distinguish between "semi-autonomous navigation", which they regard as somewhat blindly following a preprogrammed path, versus "fully autonomous navigation" in which the vehicle has the ability to observe and adapt to its environment, for instance recognizing and maneuvering around obstacles that are encountered unexpectedly. Any of these operational variants are considered to be within the scope of the present invention.

Example

Figure 19:
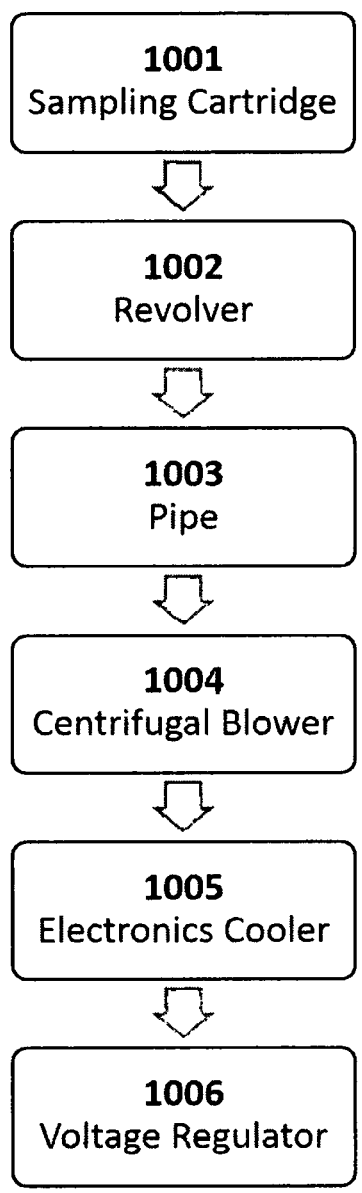
FIG. 19 is a flow chart showing the sequence by which air passes through the system in accordance with one aspect of the invention.

Comparing the air flow diagram, FIG. 19 to the mechanical diagram, FIG. 3, shows how the invention uses the blower to achieve two completely separate operations, viz., drawing air through the sample cartridge via intake pipe 8 and providing forced cooling for some of the on board electronics via exhaust structure 32.

Having the regulator 31 placed in the exhaust airflow from the blower 11 allows for the regulator to run cooler which in turn increases the reliability. The cooling from the exhaust is especially important when the Intex Quick-Fill 080 blower is operating constantly and not being run intermittently (longer than 2 minutes).

In addition to keeping the regulator cool, this design further allows the user to keep the voltage regulator on the blower attachment, which reduces the need to keep an extra voltage regulator on the sUAS when the blower assembly is not attached. Having the voltage regulator on the blower attachment keeps all the necessary systems onboard, allowing for blower attachments to be moved between different sUAS.

It should be noted that the blower 11 could run directly from the battery. This would eliminate the need for a voltage regulator, but only provided that the motor is rated for the battery's output.

Example

Each sampling cartridge 10 is preferably fixed with a unique identifier (typically a serial number, barcode, or RFID tag). When the sampling cartridge is loaded onto the sampling revolver the pilot logs the cartridge's specific position in the rotary cartridge holder 14. Once the drone is airborne and collecting the geographical location through the GPS or other geolocation means, a sample is taken by activating the blower. The unique identifier is then used to reference which sample was collected at the given geographical location. The sample is then sent to the lab for analysis and the information that is recorded is entered into a database which correlates the geolocation and lab information.

Example

Future designs using a magazine style cartridge would reduce the amount of potential error from manually recording the position of the sampling cartridge on the revolver and the possibility of indexing the incorrect cartridge on the revolver. The magazine design also reduces the amount of samples that need to have a unique identifier since only an identifier would be needed on the magazine 41 or 41' to identify it with a particular mission. In other words, the testing lab could supply the entire loaded cartridge or carousel as a single unit, and the user would return the entire unit to the testing lab, where it would be automatically unloaded, tested, and reloaded with new cartridges. The magazine design also reduces the chance of cross contamination from ground contaminants being disturbed from the rotor wash or while the operator is installing/removing the sampling cartridges.

It will be appreciated that magazines may exploit spring tension to perform the physical work of moving from one cartridge to the next. Such an approach has the further benefit of potentially reducing system mass and power requirements, because motors might be eliminated and battery draw can be reduced, as the spring can be preloaded before the flight begins and the stored mechanical energy replaces energy that otherwise would have been supplied by the battery.

Example

It will be appreciated that when a sUAS is operating completely autonomously, following a preprogrammed flight plan, there is the danger that obstacles may exist that create the hazard of collision. The invention may therefore be further modified to incorporate any suitable on-board collision avoidance system, such as those based on scanning lidar, radar, visual or ultrasonic ranging, etc., as are known in the art.

Example

The preceding examples in many cases contemplate that the sampling uses one or more sampling cartridges 10, which are generally contemplated to be single-use, disposable, or partially disposable. That is to say, when a cartridge is sent for analysis, the testing laboratory might discard the used cartridge; alternatively, it might disassemble the cartridge, remove the test article (e.g., the filter medium), and perhaps reassemble the cartridge with a new test article in a re-used housing. Thus, the amount of any cartridge that is configured or intended to be re-used may vary depending on the particular trade-offs of economics, labor, and contamination or cleaning issues that might be involved.

Example

The invention may also be configured to perform analyses in real time or near real time, by replacing the sample cartridge(s) with a test cell that can perform some physical test in the flowing air without the need to capture a sample for analysis off-line. Applicant contemplates many uses for this variant. For example, sensitive gas sensors are well known in the art, which are optimized for particular gases or vapors (e.g., ethanol, hydrogen, CO, combustible gases, etc.). Thus, the cartridge may be replaced with a flow cell in which a combustible gas sensor is operating, and the sUAS could then be used to survey an area for hazardous gas leaks (e.g., the site of a railroad accident involving tankers of volatile substances. In another contemplated application, the flow cell may include an optical scattering detector that would quantify the level of smoke, dust, water vapor, or other items of interest for applications in meteorology, environmental monitoring, regulatory compliance, and the like.

As described in the examples, an essential feature of the invention is the collection of samples at a plurality of well-defined geolocations. Although for convenience, some of the foregoing examples refer to GPS as a shorthand for geolocation information, it will be understood that the standard Global Positioning System is only one of several geolocation protocols. Furthermore, if the sUAS is operating inside of a building or enclosed space, it might be more accurate and convenient to deploy an ultrasonic triangulation system within the working space. Any suitable means for determining the location of each sample within a suitable geospatial coordinate system at an acceptable level of accuracy may be used, and all such means are considered to be within the scope of the invention.

As described in several of the examples, Applicant contemplates that the sUAS will, in general, move from place to place and then remain or loiter at selected locations for a sufficient time to collect a valid sample. The sUAS may loiter by hovering in place while the sample is collected; alternatively, the vehicle might land and collect a sample while completely stationary (e.g., at selected places on the roof of a building near air conditioning towers, etc.) For the case in which real-time or near real-time sampling is done, as in the case of continuously monitoring the atmosphere as it flows through a tube, then the loitering time may be very short in that the sUAS might be continuously moving at a low speed. In such cases, the time stamp would be associated with a geolocation that includes a volume of space defined by the speed of the vehicle and the time to collect a measurement.

| Identification of components by reference numeral | |
|---|---|
| Item | Description |
| 1 | Propeller |
| 2 | Motor |
| 3 | Frame Arm |
| 4 | Navigation and Radio |
| 5 | Controller |
| 6 | Power |
| 7 | Payload Support |
| 8 | Intake Pipe |
| 9 | Connecting Pipe |
| 10 | Sample Cartridge |
| 11 | Blower Case |
| 12 | Servo |
| 13 | Base Plate |
| 14 | Rotary Cartridge Holder |
| 15 | Ground Control |
| 31 | Voltage Regulator |
| 32 | Voltage Regulator Attached to Blower Exhaust |
| 41 | Magazine |
| 41' | Drum Magazine |
| 42 | Spring |
| 43 | Spring Plate |
| 44 | Actuator Plate |
| 45 | Actuator |
| 61 | Unloading Cartridge Telescoping Arm |
| 62 | Loading Cartridge Plate |
| 63 | Telescoping Loading Arm |
| 64 | Servo Motor Hub |
| 65 | Spring Hub |
| 66 | Unloading Carriage Plate |
| 71 | Blower Exhaust |
| 72 | Blower Intake |
| 81 | Blower Hub |
| 82 | Backward Facing Blade |
| 82' | Forward Facing Blade |
| 82" | Axial Blade |
| 121 | Shroud Attached to Blade |

I claim:

1. An atmosphere sampling system comprising:
   an unmanned rotary-wing aircraft platform comprising:
      an airframe capable of lifting a selected payload mass;
      at least one motorized rotor; and,
      a flight control system including an on-board controller;
   an atmosphere sampling unit having a total mass no greater than said selected payload mass, and comprising:
      a blower having a blade of a selected orientation, an inlet structure to draw in an atmosphere to be sampled, and an outlet to discharge said atmosphere after sampling;
      a plurality of sample containers, each having a sample collecting medium therein; and,
      an indexing means to move selected sample containers, one at a time, into contact with said inlet structure so that samples may be collected on said sample collecting medium, wherein said indexing means is selected from the group consisting of:
         a) said sample containers are held in a plate that is movable by said indexing means in two orthogonal directions to bring a selected sample container into position for sample collection, and, b) said sample containers are loaded single-file in a magazine and are moved in a stepwise manner within said magazine by said indexing means in order to bring a selected sample container into position for sample collection; and, a power supply with sufficient capacity to operate said at least one motorized rotor, said controller, said blower, and said indexing means.

2. The system of claim 1 wherein said flight control system includes said on-board controller in communication with a ground-based control station using any selected communication protocol.

3. The system of claim 1 wherein said flight control system is preprogrammed to autonomously follow a selected route and a selected sample collection schedule.

4. The system of claim 1 wherein said flight control system records geolocation data associated with each sample, so that each sample may be identified with a specific collection location.

5. The system of claim 1 wherein said power supply includes a voltage regulator.

6. The system of claim 5 wherein said voltage regulator is positioned proximate to the outlet of said blower so that air flow from said blower will remove heat from said voltage regulator.

7. The system of claim 1 further including at least one sensor selected from the group consisting of: chemical sensors; combustible gas sensors; CO sensors, hydrogen sensors, thermal sensors, hydrogen sulfide sensors, optical sensors, video cameras, microphones, IR detectors, UV detectors, optical particulate detectors, and radiation sensors.

* * * * *